(12) United States Patent  
Dmuschewsky

(10) Patent No.: US 9,526,631 B2
(45) Date of Patent: Dec. 27, 2016

(54) HOLDER FOR A MEDICAL IMPLANT

(71) Applicant: Waldemar Link GmbH & Co. KG, Hamburg (DE)

(72) Inventor: Klaus Dmuschewsky, Hamburg (DE)

(73) Assignee: Waldemar Link GmbH & Co. KG, Hamburg (DE)

( * ) Notice: Subject to any disclaimer, the term of this patent is extended or adjusted under 35 U.S.C. 154(b) by 92 days.

(21) Appl. No.: 14/427,023

(22) PCT Filed: Oct. 14, 2013

(86) PCT No.: PCT/EP2013/071444
§ 371 (c)(1),
(2) Date: Mar. 10, 2015

(87) PCT Pub. No.: WO2014/063946
PCT Pub. Date: May 1, 2014

(65) Prior Publication Data
US 2015/0245919 A1 Sep. 3, 2015

(30) Foreign Application Priority Data

Oct. 24, 2012 (EP) .................................... 12189674

(51) Int. Cl.
*A61F 2/46* (2006.01)
(52) U.S. Cl.
CPC .............. *A61F 2/46* (2013.01); *A61F 2/4603* (2013.01); *A61F 2002/4623* (2013.01); *A61F 2002/4627* (2013.01); *A61F 2002/4628* (2013.01)

(58) Field of Classification Search
CPC ................ A61F 2/46; A61F 2002/4623; A61F 2002/4624; A61F 2002/4629; A61B 17/8872
See application file for complete search history.

(56) References Cited

U.S. PATENT DOCUMENTS 6,159,215 A * 12/2000 Urbahns .............. A61B 17/025
606/86 R
6,652,533 B2 * 11/2003 O'Neil .................. A61F 2/4611
606/100

(Continued)

FOREIGN PATENT DOCUMENTS

EP 1 774 927 4/2007
WO 2005/004757 1/2005
WO 2005122970 12/2005

*Primary Examiner* — Ellen C Hammond
*Assistant Examiner* — Stuart S Bray
(74) *Attorney, Agent, or Firm* — Sand & Sebolt

(57) ABSTRACT

A holder for a medical implant having gripping and holding portions. The holding portion includes a base and at least two spaced-apart holding pins. Each pin extends axially between an outer face and free end of the base. At least one receiving opening extends between inner and outer faces of the base and tapers over at least one section. At least one first holding pin comprising a tapered axial section is inserted in the opening. A pressure surface is formed on a pin end on the inner face of the base. The section in which the opening tapers and the tapered pin axial section are such that when the pin is seated in the opening, the pin is transversely pivotable. The pressure element is movable and acts on a pressure surface portion on one side of a central axis of the pin and does not cover the central axis.

12 Claims, 2 Drawing Sheets

(56) References Cited

U.S. PATENT DOCUMENTS

| | | | | |
|---|---|---|---|---|
| 6,755,841 B2* | 6/2004 | Fraser | A61F 2/4611 | 606/99 |
| 6,902,579 B2* | 6/2005 | Harms | A61F 2/44 | 623/17.11 |
| 7,115,132 B2* | 10/2006 | Errico | A61F 2/442 | 606/247 |
| 7,118,580 B1* | 10/2006 | Beyersdorff | A61F 2/4611 | 606/99 |
| 7,223,291 B2* | 5/2007 | Errico | A61B 17/025 | 606/99 |
| 7,582,114 B2* | 9/2009 | Albert | A61F 2/442 | 606/105 |
| 7,625,380 B2* | 12/2009 | Drewry | A61B 17/025 | 606/105 |
| 7,892,239 B2* | 2/2011 | Warnick | A61F 2/4465 | 606/279 |
| 8,012,156 B2* | 9/2011 | Marquez Alvarez | A61F 2/4611 | 606/86 A |
| 8,206,399 B2* | 6/2012 | Gill | A61F 2/4425 | 606/99 |
| 8,241,294 B2* | 8/2012 | Sommerich | A61F 2/44 | 606/86 A |
| 8,382,767 B2* | 2/2013 | Wassinger | A61F 2/4611 | 606/86 A |
| 2004/0059271 A1* | 3/2004 | Berry | A61F 2/44 | 602/32 |
| 2004/0059318 A1* | 3/2004 | Zhang | A61F 2/4611 | 606/1 |
| 2004/0087947 A1* | 5/2004 | Lim | A61F 2/4465 | 606/247 |
| 2004/0102790 A1* | 5/2004 | Ralph | A61F 2/4611 | 606/99 |
| 2004/0167537 A1* | 8/2004 | Errico | A61F 2/442 | 606/99 |
| 2005/0033305 A1* | 2/2005 | Schultz | A61F 2/4425 | 606/99 |
| 2005/0090824 A1* | 4/2005 | Shluzas | A61B 17/7083 | 606/60 |
| 2005/0165408 A1* | 7/2005 | Puno | A61F 2/4611 | 606/99 |
| 2005/0234550 A1* | 10/2005 | Metz-Stavenhagen | A61F 2/44 | 623/17.11 |
| 2006/0004376 A1* | 1/2006 | Shipp | A61F 2/4611 | 606/99 |
| 2006/0167551 A1* | 7/2006 | Stad | A61F 2/4684 | 623/17.13 |
| 2006/0235426 A1* | 10/2006 | Lim | A61F 2/4465 | 606/99 |
| 2007/0123904 A1* | 5/2007 | Stad | A61F 2/4611 | 606/99 |
| 2007/0123905 A1* | 5/2007 | Schneid | A61F 2/4425 | 606/99 |
| 2008/0177299 A1* | 7/2008 | Kim | A61F 2/442 | 606/207 |
| 2008/0275455 A1* | 11/2008 | Berry | A61F 2/4611 | 606/99 |
| 2008/0287957 A1* | 11/2008 | Hester | A61B 17/025 | 606/99 |
| 2008/0306488 A1* | 12/2008 | Altarac | A61F 2/4611 | 606/99 |
| 2009/0048604 A1* | 2/2009 | Milz | A61F 2/4603 | 606/99 |
| 2009/0048673 A1* | 2/2009 | Le Huec | A61B 17/025 | 623/17.11 |
| 2009/0192611 A1* | 7/2009 | Lindner | A61F 2/44 | 623/17.11 |
| 2009/0209967 A1* | 8/2009 | Evans | A61F 2/4465 | 606/99 |
| 2009/0292361 A1* | 11/2009 | Lopez | A61F 2/446 | 623/17.15 |
| 2010/0023019 A1* | 1/2010 | Fuhrer | A61F 2/4611 | 606/99 |
| 2010/0076557 A1* | 3/2010 | Miller | A61F 2/4465 | 623/17.11 |
| 2010/0100100 A1* | 4/2010 | Refai | A61F 2/4611 | 606/99 |
| 2010/0211119 A1* | 8/2010 | Refai | A61F 2/44 | 606/86 A |
| 2010/0249795 A1* | 9/2010 | DiMauro | A61F 2/4611 | 606/99 |
| 2010/0298941 A1* | 11/2010 | Hes | A61F 2/4425 | 623/17.16 |
| 2011/0106261 A1* | 5/2011 | Chin | A61F 2/4455 | 623/17.16 |
| 2011/0202135 A1* | 8/2011 | Baek | A61F 2/4611 | 623/17.16 |
| 2011/0264152 A1* | 10/2011 | Weiman | A61F 2/4425 | 606/86 R |
| 2012/0116466 A1* | 5/2012 | Dinville | A61F 2/447 | 606/86 A |
| 2014/0135778 A1* | 5/2014 | Tipirneni | A61B 17/00491 | 606/93 |
| 2014/0350559 A1* | 11/2014 | Shea | A61F 2/30734 | 606/60 |
| 2015/0342757 A1* | 12/2015 | Lomeli | A61F 2/4684 | 623/17.16 |
| 2016/0095719 A1* | 4/2016 | Ek | A61F 2/46 | 606/86 R |

* cited by examiner

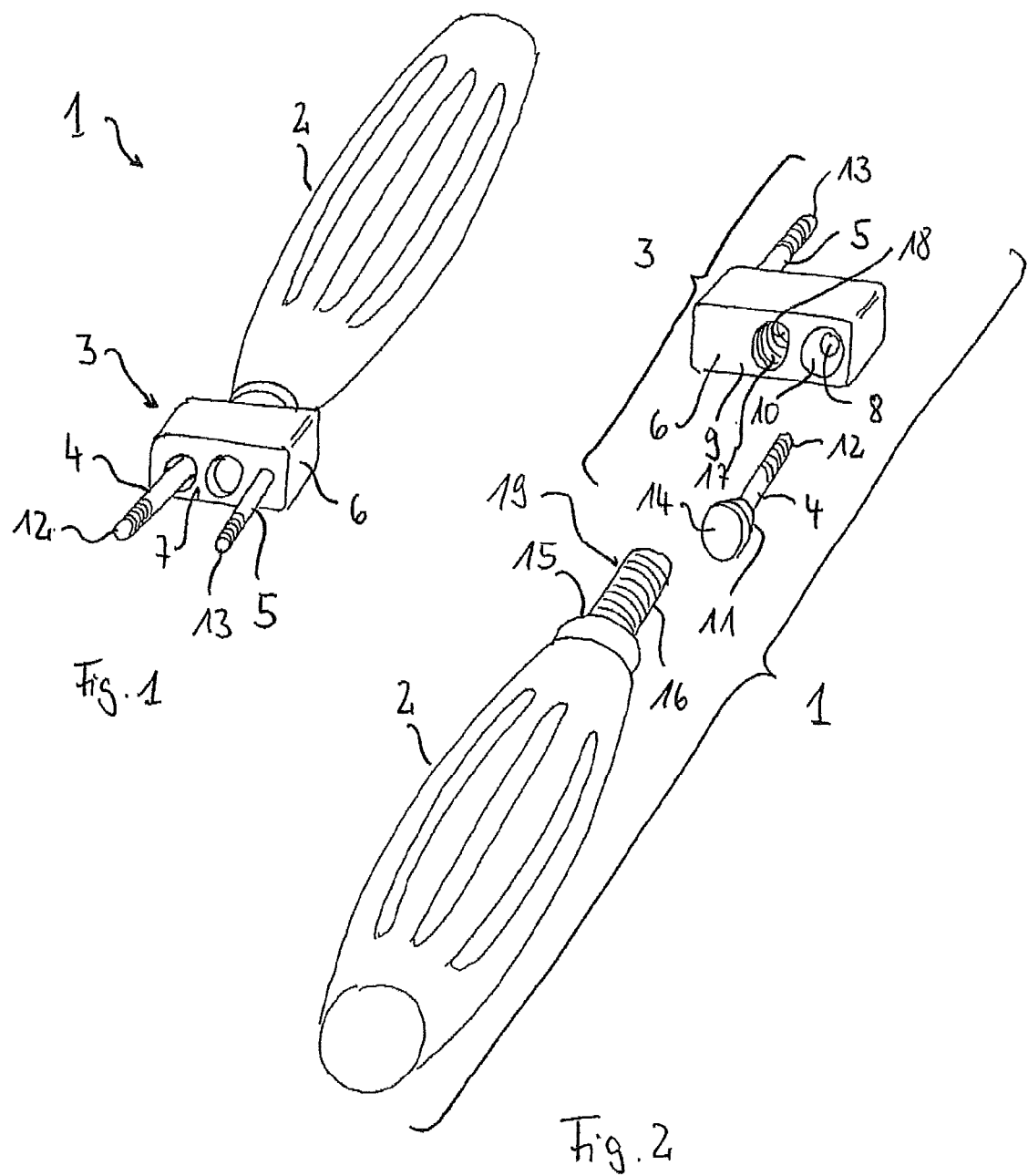

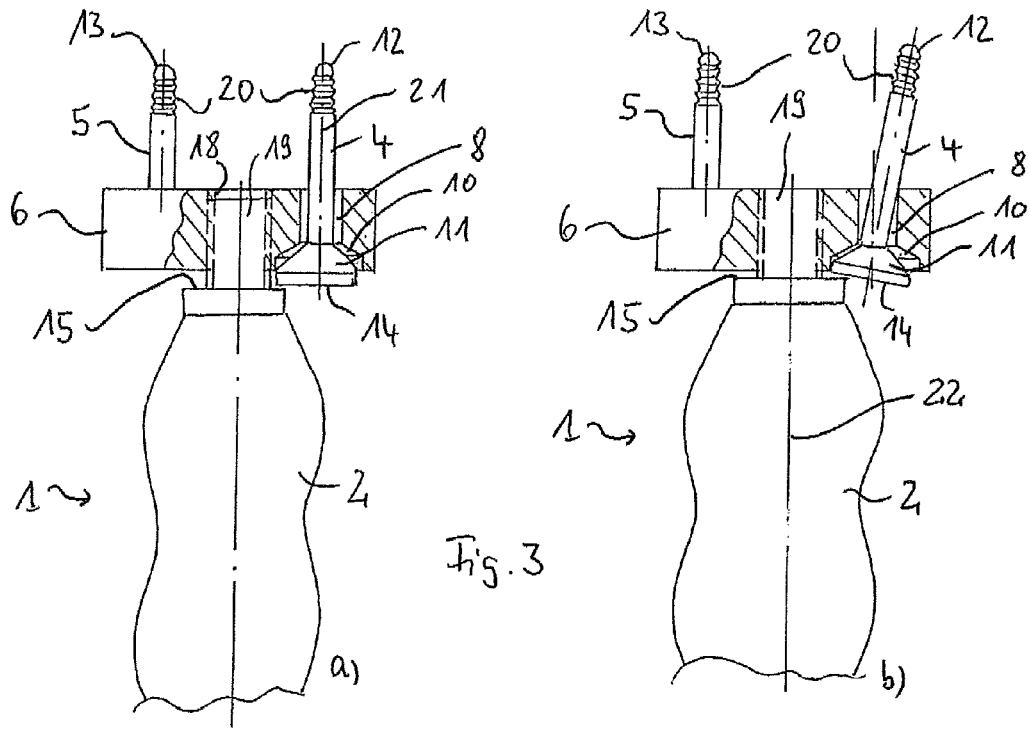
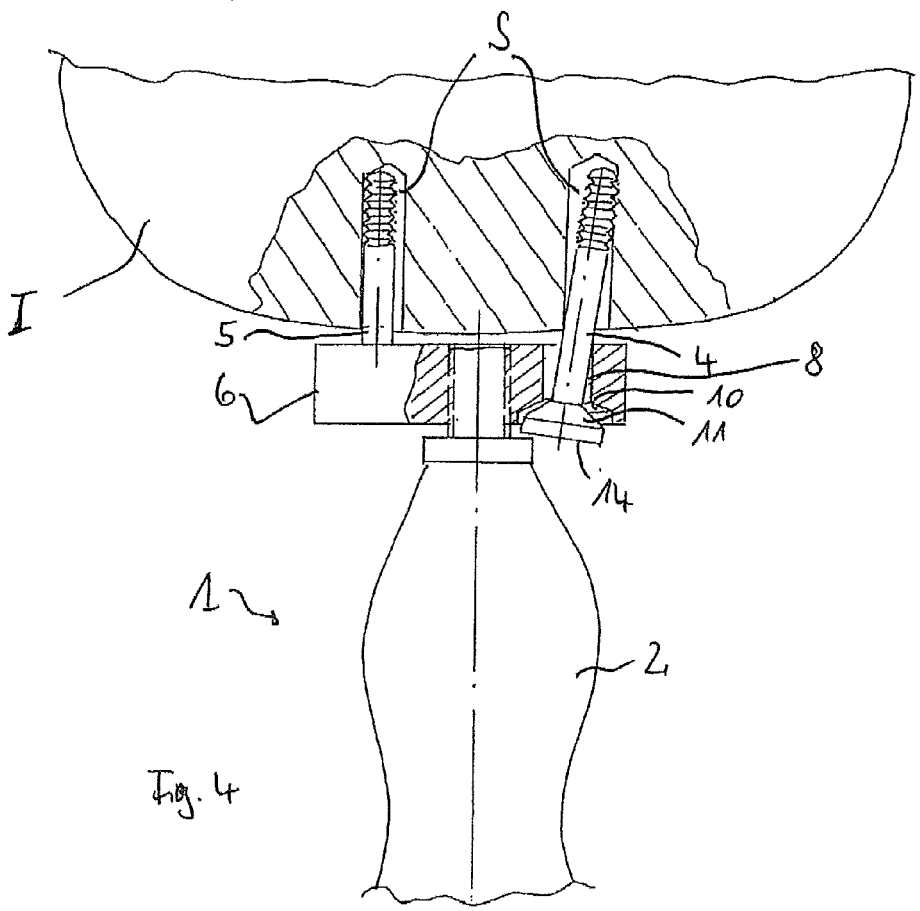

HOLDER FOR A MEDICAL IMPLANT

TECHNICAL FIELD

The present invention relates to a holder for a medical implant or a medical implant component, said holder having a gripping portion and a holding portion.

Prior Art

Such holders for medical implants are known per se. WO 2005/122970 A1, for example, discloses one example of a holder for a medical implant in the form of an artificial joint socket (which may also be interpreted to this extent as an implant component of an overall artificial joint). This holder has a holding portion in which a pressure element that can be spread by means of a tension cone can be spread outward radially. When the holder is in use, this pressure element is introduced into a joint socket and pressed against the wall of the joint socket due to the spreading by means of the spreading cone, so that it is in force-locking and optionally also formfitting contact there. This holder, in order to be used, has a gripping portion. This previously known holder is used during a surgical procedure for replacing a worn natural joint. For example, a joint socket that has been exposed and prepared (sterilized in particular) for the surgical procedure is first attached to the holding portion of the holder, the holder then also serves to correctly position the artificial joint socket in the region of a location on the bone that has been prepared for implantation, also for the insertion, i.e., driving the joint socket into the correct implant position in the bone. However, the holder may also be used in the reverse manner in a revision operation to remove a joint socket that has already been secured on the bone. To do so, the holder with its holding portion is secured on such a socket, and the socket is released from the implantation position by applying corresponding forces to the gripping portion, and can then be removed together with the holder.

Such holders are thus used for handling during a surgical procedure for positioning and/or removing implants and/or implant components. In this function, they may also be interpreted and regarded as positioning, insertion and/or extraction instruments. Likewise, however, it is also possible to use such holders in the area of preparatory treatment of a medical implant and/or a medical implant component, for example, to grip and hold such an implant and/or such an implant component in a defined manner during a sterilization procedure and/or to remove it from a sterilization basin after such a procedure.

Such a previously known holder is very specific in it use and can ultimately be used only with joint sockets or other medical implants and/or implant components having a curved interior space. Other designs of the medical implants or implant components are not compatible with such a holder, so other holders and/or holding systems must be found.

Description of the Invention

The object of the invention is to provide a remedy and to specify a corresponding holder than can be used with other medical implants or implant components. This object is achieved according to the invention by a holder for a medical implant or a medical implant component having a gripping portion and a holding portion, which holder also has and/or implements the characterizing features of a base element arranged in the holding portion; at least two holding pins spaced apart from one another in the holding portion, each extending in the axial direction up to a free end, starting from an outer face of the base element; at least one receiving opening in the base element, which penetrates the base element to the outer face from an inner face opposite its outer face, and tapers continuously over at least one section in the direction of the outer face; wherein at least one first holding pin is designed as the holding pin, inserted into the receiving opening with a clearance, having an axial section, in which it has a tapering diameter in the direction of the free end; wherein the first holding pin also has a pressure surface formed on its end located on the inner face of the base element; wherein the section in which the receiving opening tapers continuously and the axial section of the first holding pin with the tapering diameter are formed such that, when the first holding pin is seated in the receiving opening, it can be pivoted across its longitudinal axis, around a pivot point formed by the interaction of the continuously tapering section of the receiving opening and the continuously tapering axial section of the first holding pin with a tapering diameter; and a pressure element, which can be displaced in the direction of the inner face of the holding portion, and which acts on a section of the pressure surface that is located on one side of a central axis of the first holding pin and does not cover this central axis. Advantageous refinements of such a holder include that the at least two holding pins each run essentially in parallel in their respective axial direction. At least one second holding pin is fixedly connected to the base element, in particular being integrally formed with the latter. The holder may be characterized by having exactly two holding pins. The first holding pin protrudes with its pressure surface beyond the surface of the base element. The gripping portion is formed as a handle that is elongated in the axial direction and is arranged on the inner face of the base element, and the pressure element is arranged on a section of the handle, which is adjacent to the inner face of the base element, is displaceable toward the inner face of the base element and can be secured in a target position. A shoulder on the handle may be the pressure element and the handle is displaceably connectable to the base element in the axial direction of the handle, in particular via a screw connection. The handle is secured in a position on the inner face of the base element, which is located on a line connecting the points of intersection of the longitudinal axes of two holding pins with the surface of the base element on its inner face and in the middle between these points of intersection. The section in which the receiving opening tapers continuously and the axial section of the first holding pin both taper conically with a tapering diameter, wherein the axial section of the first holding pin has a smaller cone angle than the continuously tapering section of the receiving opening. In another aspect, the invention also consists of a combination, which is formed from a novel holder and a medical implant and wherein holding openings are provided in an application section on the implant and/or the implant component, these holding openings corresponding in their positioning relative to one another, their sizes and their progression to the positioning of the holding pins relative to one another, to their sizes and progressions and into which holding openings the holding pins are insertable.

According to the invention, the holder has a base element arranged in the holding portion. Furthermore, it has at least two holding pins spaced apart from one another in the holding portion, each extending in the axial direction up to a free end starting from an outer face of the base element. In addition, at least one receiving opening is provided in the base element, penetrating the base element from an inner face that is opposite its outer face as far as the outer face and tapering continuously over at least one section in the direction of the outer face. At least one first holding pin is inserted into this receiving opening in such a way that it has some clearance with respect to the receiving opening; this is in particular a clearance which is effective across the longitudinal extent of the holding pin. This first holding pin, which is inserted into the receiving opening, has an axial section, in which it has a tapering diameter in the direction of the free end, i.e., the end that protrudes beyond the outer face of the base element. The holding pin also has a pressure surface formed on its end situated on the inner face of the base element. Furthermore, the section in which the receiving opening tapers continuously, on the one hand, and the axial section of the first holding pin with the tapering diameter on the other hand, are designed so that, when the first holding pin is seated in the receiving opening, their interaction causes the first holding pin to be pivotable across its longitudinal axis around a pivot point formed by this interaction. In other words, the first holding pin, which is inserted into the receiving opening, can be pivoted and moved across its axial direction by a certain amount, so that it can assume different angular positions with respect to the surface of the outer face of the base element. Finally, the holder according to the invention also has a pressure element, which can be displaced in the direction of the inner face of the holding portion and which acts on a section of the pressure surface that is situated on one side of a central axis of the first holding pin and does not cover this central axis. This pressure element can thus apply a torque acting on the outside and on one side of the central axis of the first holding pin, which torque then acts as a tilting torque and causes a forced pivoting of the holding pin about the pivot point.

With this holder according to the invention, a medical implant or a medical implant component can be gripped and connected to the holder and thus to a gripping portion for handling before, during or after an operation. For this purpose, it is necessary only for the medical implant and/or the implant component to have the corresponding holding openings, which correspond in their arrangement relative to one another (i.e., the positioning), their direction of extent and their dimensions to the corresponding arrangements (positioning relative to one another) of the holding pins, their progressions (directions of extent) as well as dimensions (diameters in particular); namely, then the holder with the holding portion, more specifically with the holding pins protruding beyond the outer face of the base element, can be inserted into the corresponding holding openings on the medical implant and/or the implant component, and this first holding pin can be tilted about the pivot point by shifting the pressure element in the direction of the pressure surface of the holding pin and by applying a force beyond the central axis of the first holding pin, so that it is jammed in the respective holding opening. The pressure element is then secured and/or retained in such a position, and the medical implant and/or the implant component is connected securely and reliably to the holder and, for example, can be placed at the site of implantation in the human body, removed from there and the like.

One possible implant component of this type may be a plateau of an artificial knee, typically made of plastic, for example, i.e., the running surface for the femur component of this artificial joint placed on the upper side of the tibia component. With such a plateau, for example, corresponding holding openings can be easily added on an end face, so that this plateau can be gripped and held and positioned in a clamping manner, as described above, using a holder according to the invention. The use of such a holder according to the invention is of course not limited to such an example as that outlined, but other implant components which may be provided with corresponding holding openings may also be considered here.

Such a holder according to the invention is particularly simple in its mechanical design and therefore reliable in its holding effect but can also be implemented in a manner that permits particularly simple cleaning and sterilization of the instrument which is typically reusable. To be sure, more than just one (the first) holding pin can be accommodated in a respective receiving opening and designed to be pivotable accordingly, as described above. However, it has been found that this is not necessary, but it is usually sufficient to design only a single holding pin to be pivotable in this way. Additional holding pins may thus be formed as holding pins fixedly connected to the base element, in particular, as holding pins that are integrally molded thereon. In particular in the case of an integral molding, the result is no gaps or other transitions that might be problematical (because difficult to reach) in a post-operative cleaning and sterilization. The surface on the outer face of the base element, on which the holding pins protrude and beyond which they extend up to the free end, may in particular be shaped so that it allows a simple cleaning and sterilization. It may be designed to be flat and planar in particular, but it may also be adapted to the surface of an implant and/or an implant component to be gripped with the holder, for example, having an inverse curvature accordingly.

The holding pin seated in the receiving opening may, within the scope of the invention, also be connected by flexible bridges to the material of the base element. In particular, however, it is freely removable from the receiving opening, so that it can be removed and cleaned and sterilized individually for the purpose of cleaning the holder according to the invention. The remaining holder, in particular the remaining base element, can be cleaned and sterilized separately, wherein, because the receiving opening tapers continuously, there are also ideally no shoulders or edges in the receiving opening that are difficult to access for cleaning and sterilization.

In order for the holding pin, which is inserted loosely from the inner face of the base element into the receiving opening, not to fall out of it in the direction of the outer face, corresponding restraint structures are provided. In a preferred embodiment, it is sufficient here to use for such a restraint the sections (structures), which already interact with one another, to form the pivot bearing in the receiving opening and on the holding pin, in which the receiving opening and also the diameter of the holding pin each taper. This is because, in addition to a pivot point, these sections and/or structures also interact to form a restraint the first holding pin and a stop against any further longitudinal movement of this first holding pin in the receiving opening in the direction of the outer face of the base element.

The holder according to the invention can be used particularly easily if the holding pins run essentially parallel in their respective axial direction. This path is understood in particular to mean the resulting path in the region from the surface of the base element on the outer face up to the free ends of the holding pins. The paraphrase "essentially parallel" here also takes into account the fact that the first holding pin seated in the receiving opening in the base element permits and/or experiences a pivoting across its axial direction, so that the alignment of its axial direction is variable. This means that in a possible pivot position of the first holding pin, its longitudinal axis is actually aligned in parallel with the longitudinal axes of the additional holding pins, whether these are stationary or are also pivotable in a receiving opening. Such a parallel alignment allows a particularly simple insertion of the holding pins into corresponding holding openings that are also aligned in parallel on the medical implant and/or the medical implant component.

The medical holder may, in principle, have several holding pins, in particular more than two. However, it is sufficient for many applications if it has exactly two holding pins. In this respect, such an embodiment is also preferred because, on the one hand, with a larger number of holding pins, correspondingly more holding openings must be provided on the medical implant and/or the implant component, which may, in principle, weaken the implant component structurally, and which also requires a larger space and/or a larger area, in which and/or across which the holding openings are introduced. Secondly, holding pins, and thus holding openings to be provided in the implant and/or in the implant component, require a greater measure of dimensional stability and reduce the admissible tolerances. In a particular preferred and simple, preferred embodiment, the holder according to the invention has precisely two holding pins, one of which, namely the first holding pin, is seated in the respective receiving opening and is pivotable accordingly, while the other, the second holding pin is fixedly connected to the base element. In this embodiment, the two holding pins are preferably designed with their longitudinal axes essentially parallel and thus yield a type of "holding fork."

With the holder according to the invention, the first holding pin can advantageously protrude with its pressure surface beyond the surface of the base element. In such an embodiment, the pressure element may be designed to be flat and planar and may press with one part against the pressure surface and with another part against the surface of the base element on its inner face. However, if the pressure surface of the first holding pin is countersunk in the receiving opening, which, in principle, is also possible, then the pressure element must protrude like a mandrel into the receiving opening, which is unfavorable in the transmission of greater forces in particular, such as those forces required for the implementation and/or application of corresponding clamping forces to a holding opening formed in the medical implant and/or in the implant component. A broad and extensive surface of the pressure element acting on the pressure surface, such as that which is possible with a pressure surface of the first holding pin protruding beyond the surface of the base element on the inner face, is more favorable than a mandrel-type pressure element, which must penetrate into the receiving opening in the base element and must exert its effect there.

In one advantageous embodiment, the handle of the holder according to the invention may be formed as a handle that is elongated in one axial direction and is arranged on the inner face of the base element, wherein the pressure element is then preferably arranged on a section of the handle adjacent to the inner face of the base element and is displaceable in the direction of the inner face of the base element and securable in a target position. This interaction between the pressure element and the handle can be achieved in a particularly simple manner if a shoulder formed on the handle protrudes and/or acts in the direction of the inner face of the base element, and furthermore, if the handle can be connected to the base element, so that it is displaceable on the whole in the axial direction of the handle. Such connectability can be implemented, in particular, by a screw connection, for example, an inner thread in the base element and an outside thread on the handle. Thus, by screwing in the handle in the direction of the base element, in particular in the direction of the surface on its inner face, the shoulder can be pressed against the pressure surface of the first holding pin, and a high pressing force can be applied to create a sufficiently high clamping force in the pivoting displacement of the first holding pin.

The position in which the handle is secured on the inner face of the base element, i.e., in which its longitudinal axis intersects with the surface of the base element, may lie in particular on a connecting line of the points of intersection of the longitudinal axes of two holding pins with the surface of the base element on its inner face, preferably at the center between these points of intersection. In particular, the point of intersection of the longitudinal axis of a holding pin that is pivotable in its axial direction with the surface of the base element on its inner face is variable due to the pivotability within a frame. In particular, the point of intersection in this case should be defined as the point that is established in a preferred alignment of the holding pin for the insertion of same into a holding opening on the medical implant and/or on the implant body. In particular, this may be such an alignment in which the holding pins are aligned in parallel with one another in their axial direction.

Such an arrangement yields a symmetrical arrangement, on the one hand, but, on the other hand, means that the pressure element, which is displaceable along the axis of the longitudinal extent of the handle in the direction of the surface on the inner face of the base element, acts on a side of the first holding pin facing the neighboring holding pin, so that it pivots the latter outward with its free end protruding beyond the outer face when a compressive force is applied, i.e., away from the neighboring holding pin, and thus applies an outwardly directed clamping force. Such an outwardly directed clamping force is often more favorable for reliable gripping and holding.

The sections, which form a pivot point in their interaction (i.e., the section in which the receiving opening tapers continuously and the axial section of the first holding pin with a tapering diameter) may have completely different shapes. For example, these may be spherically shaped sections with a partially spherical receptacle in the receiving opening and a corresponding partial sphere on the holding pin, which are coordinated with one another in their diameters in order to achieve the formation of a pivot point, as described here. However, each section may in particular also be designed to have a conical taper. Then, different cone angles must be selected so as not to obtain an exact conical seating, which is defined across the longitudinal axis of the first holding pin. In particular, the axial section of the first holding pin should have a smaller cone angle than the continuously tapering section of the receiving opening. Thus, one section of the pin having a steeper flank is seated in a section of the receptacle having walls that slope more shallowly, which leads to a corresponding possibility of movement acting across the longitudinal direction of the holding pin, i.e., a pivot point. A "pivot point" within the meaning of the invention is not to be understood as one that is necessarily in a fixed position for the pivoting movement. It may also travel and change its position during a movement operation. Of sole importance is that a bearing of the holding pin in a central section is achieved and by the interaction of the conically tapering sections of the receiving opening and of the holding pin, so that the application of a tilting torque to the holding pin on its one end that is provided with the pressure surface in the one direction produces a tilting of the free end in an opposite direction along the original alignment of its longitudinal axis.

BRIEF DESCRIPTION OF THE DRAWINGS

Additional advantages and features of the invention are derived from the following description of an exemplary embodiment on the basis of the accompanying figures, in which:

FIG. 1 shows a perspective view of an exemplary embodiment of a holder according to the invention in a view obliquely from the front, FIG. 2 shows in an exploded diagram, the holder according to the invention, as in FIG. 1, with its individual components, FIG. 3 shows in two diagrams a) and b), the corresponding holder according to FIG. 2 in two different positions before spreading of the holding pins (FIG. 3*a*) and with the holding pin spread (FIG. 3*b*) for clamping an implant gripped with the holder, and FIG. 4 shows in another diagram, the holder according to the invention in the embodiment according to FIG. 1, in cooperation with a medical implant gripped with and secured on this holder.

The figures show schematic drawings of an exemplary embodiment for a holder according to the invention. The figures are basic diagrams illustrating the embodiment according to the invention in particular with regard to the design features that are essential to the invention. However, these diagrams are by no means to be understood as true to scale or as full-quality construction drawings. They also depict just one exemplary embodiment of a plurality of possible embodiment variants of a holder according to the invention.

The figures show in various diagrams an exemplary embodiment of a holder according to the invention, which, in general, is labeled therein with reference numeral 1. The holder 1, which is described basically first with reference to FIGS. 1 and 2, includes a gripping portion 2, in this case an axially elongated handle, as well as a holding portion 3, which is connected in a front area to the gripping portion 2. In the holding portion 3, two holding pins 4 and 5 protrude on a side, namely the outer face 7, opposite the gripping portion 2, and end in free ends 12 and/or 13. These holding pins 4 and 5 are arranged and/or secured on a base element 6.

As can be seen in the exploded diagram according to FIG. 2 in particular, the holding pins 4 and 5 are of different types. Whereas the holding pin in this exemplary embodiment is integrally formed with the base element 6, and is thus fixedly mounted on the outer face 7 with a predefined and non-variable axial extent with respect to the alignment of the base element 6, the holding pin 4 is releasably inserted into a receiving opening 8, which penetrates the base element 6 from an inner face 9 to the outer face 7. The receiving opening 8 is formed in a section 10 with a diameter that tapers conically in the direction of the outer face 7. In this exemplary embodiment, this section 10 begins on the inner face 9, where the receiving opening 8 has a larger diameter, and it extends from there in the direction of the outer face 7 up to a tapering diameter of the receiving opening 8, which is then continued (cf. also FIGS. 3*a* and 3*b* in this regard).

The holding pin 4 that is releasably inserted into this receiving opening 8 also has a section 11 having a conically tapering diameter. It also has a pressure surface 14 on its side opposite the free end 12.

On its end facing the base element 6, the gripping portion 2 has a cone-shaped section 19, which is provided with an outside thread 16. This section 19 transitions into the remaining gripping portion 2 via a protrusion 15 which forms a pressure surface. Another opening, the screw opening 18, is formed at the center of the base element 6 and is provided with an inside thread 17. In its axial extent, the screw opening 18 here runs essentially parallel to the receiving opening 8. When joining the holder 1, which is thus formed from a total of three individual parts, namely the gripping portion 2, the base element 6 with the holding pin 5 integrally molded thereon and the holding pin 4 releasably inserted into the receiving opening 8, the holding pin 4 is first inserted into the receiving opening 8, through which it is unable slip to the outer face 7 of the base element 6 due to the interaction of the sections 10 and 11. The cone-shaped section 19 is then inserted into the screw opening 18 and the gripping portion 2 is screwed to the base element 6.

FIG. 3 illustrates in diagrams a and b the situation that results in the last remaining part of the path of screwing the cone-shaped [section] 19 of the gripping portion 2 into the screw opening 18. It can first be seen here that the tapering section 11 of the holding pin 4 has a conical design, just like the tapering section 10 of the receiving opening 8. However, the cone angles in this case differ from one another. The cone angle of the section 11 is steeper than the cone angle of the section 10, so that the section 11, and thus the holder pin 4, is able to move in a tilting manner with respect to the section 10, and thus the receiving opening 8.

Furthermore, it can be seen that when the cone-shaped section 19 is screwed into the screw opening 18, the protrusion 15 protrudes beyond the pressure surface 14 into a region on one side of a central axis 21 of the holding pin 4. If the gripping piece 2 with its cone-shaped section 19 is then screwed further into the screw opening 18, starting from FIG. 3*a*, then the protrusion 15 on the gripping piece 2 will strike the pressure surface 14 of the holding pin 4 further and drive the holding pin 4 with its free end 12 outward starting from a central axis 22 of the holder 1, enabled by the clearance of the holding pin in the receiving opening 8, and due to the differently formed cone angles in sections 11 and 10.

FIG. 4 shows how this technical effect is utilized to detect and clamp a medical implant I. Blind holes S are added in the implant 1, fitting the spacing between pins 4 and 5 and corresponding to their essentially parallel longitudinal extent in a resting position. The holding pins 4, 5 are inserted into these blind holes in a state like that shown in FIG. 3*a*. The holding pin 4, as shown in FIG. 3*b* and as described on the basis of this diagram, is then tilted and forced outward by screwing the gripping portion 2 with its cone-shaped section 19 further into the screw opening 18 and through the resulting interaction of the protrusion 15 with the pressure surface 14. The holder 1 clamps its holding pins 4, 5 in the blind holes S in this way, and the medical implant I is securely attached to and held by the holder 1. To increase the holding force, fluting 20 is introduced into the region of the free ends 12, 13 of the holding pins 4, 5.

With the medical implant I thus attached to the holder, for example, a plateau made of plastic, for example, PE, for the tibia component of an artificial knee joint, this implant can be moved to its implantation site and placed there as well as being held there until it is anchored. Once the implant I has been securely attached, the contact between the protrusion 15 and the pressure surface 14 is released by unscrewing the gripping portion 2 with its cone-shaped section 19 out of the screw opening 18, so that the holding pin 4 can be tilted back in the direction of its original alignment, in which it runs with its longitudinal axis essentially parallel to the longitudinal axis of the holding pin 5 and the clamping is released. The holder 1 can then be removed. In the same way, the holder 1 can of course be used to remove an implant I from an implantation site in conjunction with a revision surgery. Then the holder 1 is attached as described above to the implant, which is still in the implantation position, the implant I is released and removed and, after this removal, the holder 1 is released from the implant I, as described above.

After a use, the holder according to the invention can be cleaned and disinfected in a particularly simple manner because it consists of only three parts, namely the gripping portion 2, the base element 6 with the holding pin 5 integrally molded thereon, as well as the holding pin 4 seated releasably in the receiving opening 8. All these parts are formed without any recesses that are difficult to access, and therefore they are easy to reach for cleaning tools such as brushes, without fear of impurity residues.

LIST OF REFERENCE NUMERALS

1 Holder
2 Gripping portion
3 Holding portion
4 Holding pin
5 Holding pin
6 Base element
7 Outer face
8 Receiving opening
9 Inner face
10 Section
11 Section
12 Free end
13 Free end
14 Pressure surface
15 Protrusion
16 Outside thread
17 Inside thread
18 Screw opening
19 Cone-shaped section
20 Fluting
21 Central axis
22 Central axis
I Implant
S Blind hole

The invention claimed is:

1. A holder for a medical implant or a medical implant component having a gripping portion and a holding portion, wherein said holder comprises:
   a. a base element arranged in the holding portion;
   b. at least two holding pins spaced apart from one another in the holding portion, each holding pin extending in an axial direction up to a free end starting from an outer face of the base element;
   c. at least one receiving opening in the base element which penetrates the base element from an inner face to the outer face where the inner face is opposite the outer face, and wherein the at least one receiving opening tapers continuously over at least one section in the direction of the outer face;
   wherein a first holding pin of the at least two holding pins is inserted into the receiving opening with a clearance, and the first holding pin has an axial section which has a tapering diameter in the direction of the free end;
   wherein the first holding pin also has a pressure surface formed on an end located on the inner face of the base element; and
   wherein the at least one section, in which the receiving opening tapers continuously and the axial section of the first holding pin with the tapering diameter are formed such that, when the first holding pin is seated in the receiving opening, the first holding pin is pivotable across its longitudinal axis, around a pivot point formed by the interaction of the continuously tapering section of the receiving opening and the at least one continuously tapering axial section of the first holding pin with a tapering diameter; and
   d. a pressure element which is displaceable in the direction of the inner face of the holding portion and which acts on a section of the pressure surface that is located on one side of a central axis of the first holding pin and does not cover this central axis.

2. The holder according to claim 1, wherein the at least two holding pins each run generally in parallel in their respective axial direction.

3. The holder according to claim 1, wherein a second holding pin of the at least two holding pins is fixedly connected to the base element.

4. The holder according to claim 1 wherein there are exactly two holding pins.

5. The holder according to claim 1, wherein the first holding pin protrudes with its pressure surface beyond a surface of the base element.

6. The holder according to claim 1, wherein the gripping portion is formed as a handle that is elongated in the axial direction and is arranged on the inner face of the base element, and the pressure element is arranged on a section of the handle which is adjacent to the inner face of the base element and is displaceable toward the inner face of the base element and is securable in a target position.

7. The holder according to claim 6, further comprising a shoulder on the handle as the pressure element and wherein the handle is displaceably connectable to the base element in an axial direction of the handle.

8. The holder according to claim 5, wherein the handle is secured in a position on the inner face of the base element which is located on a line connecting points of intersection of the longitudinal axes of two holding pins with the surface of the base element on its inner face and in the middle between these points of intersection.

9. The holder according to claim 1, wherein the section in which the receiving opening tapers continuously and the axial section of the first holding pin both taper conically with a tapering diameter, wherein the axial section of the first holding pin has a smaller cone angle than the continuously tapering section of the receiving opening.

10. A combination consisting of a holder according to claim 1 and a medical implant or a medical implant component, wherein holding openings are provided in an application section on the medical implant or the medical implant component, these holding openings corresponding in their positioning relative to one another, their sizes and their progression to the positioning of the at least two holding pins relative to one another, to sizes and progressions of the at least two holding pins and into which holding openings the at least two holding pins are insertable.

11. The holder according to claim 3, wherein the second holding pin is integrally formed with the base element.

12. The holder according to claim 7, wherein the handle is displaceably connectable to the base element in the axial direction of the handle via a screw connection.

* * * * *